US012808088B2

(12) United States Patent
Yoshioka et al.

(10) Patent No.: US 12,808,088 B2
(45) Date of Patent: Nov. 24, 2026

(54) BEHAVIOR CONTROL METHOD AND SPINNING POSITION CONTROL METHOD FOR BAGWORMS

(71) Applicants: NATIONAL AGRICULTURE AND FOOD RESEARCH ORGANIZATION, Tsukuba (JP); KOWA COMPANY, LTD., Nagoya (JP)

(72) Inventors: Taiyo Yoshioka, Tsukuba (JP); Tsunenori Kameda, Tsukuba (JP); Akimune Asanuma, Tsukuba (JP); Norihiko Fukuoka, Tsukuba (JP)

(73) Assignees: NATIONAL AGRICULTURE AND FOOD RESEARCH ORGANIZATION, Tsukuba (JP); KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 18/246,733

(22) PCT Filed: Sep. 30, 2021

(86) PCT No.: PCT/JP2021/036079
§ 371 (c)(1),
(2) Date: Mar. 27, 2023

(87) PCT Pub. No.: WO2022/071480
PCT Pub. Date: Apr. 7, 2022

(65) Prior Publication Data

US 2023/0287599 A1 Sep. 14, 2023

(30) Foreign Application Priority Data

Sep. 30, 2020 (JP) ................................ 2020-164314

(51) Int. Cl.
*D01B 7/06* (2006.01)
*A01K 67/35* (2025.01)

(52) U.S. Cl.
CPC ............... *D01B 7/06* (2013.01); *A01K 67/35* (2025.01); *D10B 2211/04* (2013.01)

(58) Field of Classification Search
None
See application file for complete search history.

(56) References Cited

U.S. PATENT DOCUMENTS 11,926,927 B2 * 3/2024 Yoshioka ................ D04H 1/09
2010/0068517 A1 * 3/2010 Liu .......................... D01B 7/00
428/401

(Continued)

FOREIGN PATENT DOCUMENTS

JP 2018197415 A 12/2018
JP 2019116701 A 7/2019

(Continued)

OTHER PUBLICATIONS

Flaherty, Joseph, "A mind-blowing dome made by 6500 computer-guided silkworms", Design WIRED.com (Jul. 11, 2013) https://www.wired.com/2013/07/your-next-3-d-printer-might-be-filled-with-worms/ (Year: 2013).*

(Continued)

*Primary Examiner* — Katelyn T Truong
(74) *Attorney, Agent, or Firm* — Lucas & Mercanti, LLP

(57) ABSTRACT

A movement control method and a spinning position control method for a bagworm is provided, in which a bagworm is led to a predetermined position and allowed to spin a foothold silk thread at the predetermined position. A behavior control method in which a light is radiated to a bagworm to lead the bagworm toward a direction from which the light is radiated, and a spinning position control method in which (Continued)

a light is radiated to a bagworm at a spinning position on a surface of a base material to allow the bagworm to spin at the position are also provided.

11 Claims, 6 Drawing Sheets

(56) References Cited

U.S. PATENT DOCUMENTS

| | | | | |
|---|---|---|---|---|
| 2019/0000061 | A1 | 1/2019 | Shimoda et al. | |
| 2020/0325606 | A1* | 10/2020 | Hardy | D01B 7/00 |
| 2021/0372007 | A1 | 12/2021 | Yoshioka et al. | |

FOREIGN PATENT DOCUMENTS

| | | | |
|---|---|---|---|
| KR | 101275688 | B1 | 6/2013 |
| WO | 2012165477 | A1 | 12/2012 |
| WO | 2017022333 | A1 | 2/2017 |

OTHER PUBLICATIONS

Patrick, Will "Experiment: Design with Silkworms", Autodesk Instructables https://www.instructables.com/Experiment-Designing-with-silkworms/ Note: comments made from "9 years ago" captured on Aug. 5, 2024, therefore available in 2015 (Year: 2015).*

Kitabatake, Seiji et. al. "Wavelength-dependent properties of phototaxis in larvae of Bombyx mori" Photochemistry and Photobiology vol. 37, pp. 321-327.Wiley Online Library (Jul. 1982) https://onlinelibrary.wiley.com/doi/epdf/10.1111/j.1751-1097.1983.tb04480.x (Year: 1983).*

Costa, Joao, et. al. "Silk Pavilion II", 2020 (Wayback Machine Jul. 9, 2020) https://oxman.com/projects/silk-pavilion-ii (Year: 2020).*

Harvard University "Light controls a worm's behavior: Scientists commandeer organism's nervous system without wires or electrodes" Science Daily (Jan. 23, 2011) https://www.sciencedaily.com/releases/2011/01/110118143222.htm (Year: 2011).*

JP 2019116701 A Machine translation of the description from Espacenet (Year: 2019).*

Osaki, "Animals Teach Science on Natural Fibers:—Spider's Silks, Bagworm's Silks, and Collagen Fibers-", Journal of the Society of Fiber Science and Technology, 2002, vol. 58, No. 3, pp. 74-78, Partial English Translation 3 pages.

Kuwana et al., "High-Toughness Silk Produced by a Transgenic Silkworm Expressing Spider (Araneus ventricosus) Dragline Silk Protein", Plos One, 2014, vol. 9, Issue 8, e105325, pp. 1-11.

International Search Report and Written Opinion for Corresponding International Application No. PCT/JP2021/036079, 6 pages, Nov. 2, 2021.

EPO, Supplementary European Search Report, mailed Sep. 6, 2024, issued for the related European patent application No. 21875776.3, 5 pages.

Shimizu Isamu et al., "Phototactic Behavior in the Silkworm, Bombyx mori. II", Environment Control in Biology, vol. 19 (1981) Issue 3, Sep. 30, 1981, pp. 1-9, with partial English translation.

* cited by examiner

A

B

A

B

BEHAVIOR CONTROL METHOD AND SPINNING POSITION CONTROL METHOD FOR BAGWORMS

CROSS-REFERENCE TO RELATED APPLICATIONS

This application is a 371 of PCT/JP2021/036079, filed Sep. 30, 2021, which claims the benefit of Japanese Patent Application No. 2020-164314, filed Sep. 30, 2020.

TECHNICAL FIELD

The present invention relates to a method of controlling the behavior of a bagworm or a method of controlling a spinning position of a bagworm, and to a bagworm silk thread-producing apparatus using the methods.

BACKGROUND ART

The term "bagworm" collectively refers to a moth larva belonging to the family Psychidae in the order Lepidoptera. It is known that a bagworm usually spends the whole larval stages living in a spindle-shaped or cylinder-shaped nest (bag nest) made of pieces of leaves and twigs assembled by a thread spun by the bagworm itself, during which the larva hides inside the nest and moves with the nest even for eating. The bagworm silk thread spun by the bagworm has recently been attracting attention as a very useful new animal-fibrous natural material.

However, for the practical application of such a bagworm silk thread, several problems still have to be solved. One of the problems is that no long bagworm silk thread is obtainable. A bagworm pupates in its nest where the bagworm spends its life in the larval stage, and therefore spins no cocoon for pupation. Additionally, a nest of a bagworm is extended as the bagworm grows from the first instar in principle, and old and new silk threads are mixed together in the nest. The silk threads are fragmented and discontinued in the nest. That is, a bagworm nest itself is assembled with relatively short silk threads entangled with each other, and thus, a long fiber cannot be obtained from the nest by any conventional method. For this reason, it is hitherto difficult to put a bagworm silk thread to practical use.

This problem has so far been solved by a method of collecting a foothold silk thread of a bagworm silk thread in long form, the method developed by the present inventors (Patent Literature 1). A foothold silk thread is a bagworm silk thread preliminarily spun in the direction of movement to be used as a scaffold for preventing the bagworm from falling from a branch or the like. A foothold silk thread is spun in a zigzag pattern, and besides, the behavior of a bagworm itself is difficult to control. The movement of a bagworm is up to the insect, and thus, the forward and backward movement of a bagworm causes a bagworm silk thread to be complicatedly folded even severalfold one on another. As a result, such a bagworm silk thread is conventionally difficult to collect. In the thread-collecting method, a bagworm is placed on a rail having a specific width, and the behavior of the bagworm is thereby controlled. The method is successful in mass-producing a long bagworm silk thread stably. However, for a bagworm silk thread to be spun at a predetermined position on the surface of, for example, a three-dimensional structure other than a rail, there is still no method in which a bagworm is led to the predetermined position and allowed to spin. For this reason, establishing a method of controlling the behavior of a bagworm is imperative for the practical application of a bagworm silk thread.

CITATION LIST

Patent Literature

Patent Literature 1: WO2012/165477

Non-Patent Literature

Non-Patent Literature 1: Shigeyosi Ohsaki, 2002, Sen'i Gakkaishi (Sen'i To Kogyo), 58:74-78

Non-Patent Literature 2: Kuwana Y, et al., 2014, PLOS One, DOI: 10.1371/journal.pone.0105325

SUMMARY OF INVENTION

Technical Problem

An object of the present invention is to develop and provide a method of controlling the behavior of a bagworm. An additional object is to develop and provide a method of obtaining a bagworm silk thread efficiently.

Solution to Problem

To solve the above-mentioned problems, the present inventors have made studies vigorously, and as a result, have discovered that a bagworm has phototaxis, that is, a characteristic by which, when a light is radiated to a bagworm, the bagworm moves toward a direction from which the light is radiated. When the direction of light radiation is changed, the migration direction of the bagworm is changed to the new direction of light radiation after the change. The present inventors have made it clear that such phototaxis strongly acts in response to a specific wavelength light. On the other hand, the present inventors have also discovered a characteristic which is conventionally not known at all, that is, a characteristic by which the spinning behavior of a bagworm is led by a wavelength light different from the wavelength light having high phototaxis. Utilizing these characteristics makes it possible to freely control the behavior of a bagworm, the behavior being hitherto difficult to control, and enables a bagworm to spin at a desired position. The present invention is based on these new findings, and will provide the following items.

(1) A method of controlling a behavior of a bagworm, comprising a process of radiating a behavior control light to the bagworm to lead the bagworm toward a direction from which the light is radiated.

(2) The method of controlling the behavior according to (1), wherein a wavelength of the behavior control light is 405 nm±60 nm.

(3) The method of controlling the behavior according to (1) or (2), comprising a process of changing a direction of leading of the bagworm by changing the direction from which the light is radiated.

(4) The method of controlling the behavior according to any one of (1) to (3), which is performed under a light-shielding condition.

(5) A method of controlling a spinning position of a bagworm, comprising a process of radiating a spinning position control light to the bagworm from a predetermined position on a base material to allow the bagworm to spin at the position.

(6) The method of controlling the spinning position according to (5), wherein a wavelength of the spinning position control light is 560 nm±150 nm.

(7) The method of controlling the spinning position according to (5) or (6), comprising a process of radiating a behavior control light having a wavelength of 405 nm±60 nm to the bagworm from the predetermined position on the base material to lead the bagworm to the position.

(8) The method of controlling the spinning position according to any one of (5) to (7), which is performed under a light-shielding condition.

(9) The method of controlling the spinning position according to any one of (5) to (8), wherein the base material is a three-dimensional structure.

(10) The method of controlling the spinning position according to any one of (5) to (9), wherein the base material is a transparent base material or a translucent base material.

(11) A method of producing a thread mass of a bagworm silk thread obtained using the method of controlling the spinning position of the bagworm according to any one of (5) to (10).

(12) A bagworm silk thread-producing apparatus comprising one or a plurality of light sources that can radiate a spinning position control light from any direction to a base material on which a bagworm is allowed to spin.

(13) The apparatus according to (12), wherein a wavelength of the spinning position control light is 560 nm±150 nm.

(14) The apparatus according to (12) or (13), further comprising one or a plurality of light sources that can radiate a behavior control light having a wavelength of 405 nm±60 nm from any direction to the base material.

(15) The apparatus according to any one of (12) to (14), wherein the light sources are movable.

(16) The apparatus according to any one of (12) to (15), comprising a housing having a light-shielding environment in the apparatus.

(17) Use of a light source that can radiate a light having a wavelength in a range of 405 nm±60 nm for controlling a behavior of a bagworm.

(18) Use of a light source that can radiate a light having a wavelength in a range of 560 nm±150 nm for controlling a spinning position of a bagworm.

The present specification encompasses the contents disclosed in the specification and/or drawings of Japanese Patent Application No. 2020-164314, on which the priority of the present application is based.

Advantageous Effects of Invention

A method of controlling a behavior of a bagworm according to the present invention makes it possible to lead the bagworm to a predetermined position.

A method of controlling a spinning position of a bagworm according to the present invention makes it possible to allow the bagworm to spin a foothold silk thread at a predetermined position, thus obtaining a bagworm silk thread efficiently.

A bagworm silk thread-producing apparatus according to the present invention makes it possible to embody the method of controlling the spinning position of the bagworm according to the present invention.

BRIEF DESCRIPTION OF DRAWINGS

FIG. 4A is a conceptual diagram of the whole testing device. In addition, FIG. 4B is a schematic diagram for describing the internal faces of a cage in which bagworms are placed, in the testing device shown in FIG. 4A.

FIG. 5A shows an overview of the testing device. In addition, FIG. 5B shows the inside of the cage in which 10 bagworms were placed on the bottom face.

DESCRIPTION OF EMBODIMENTS

Figure 1:
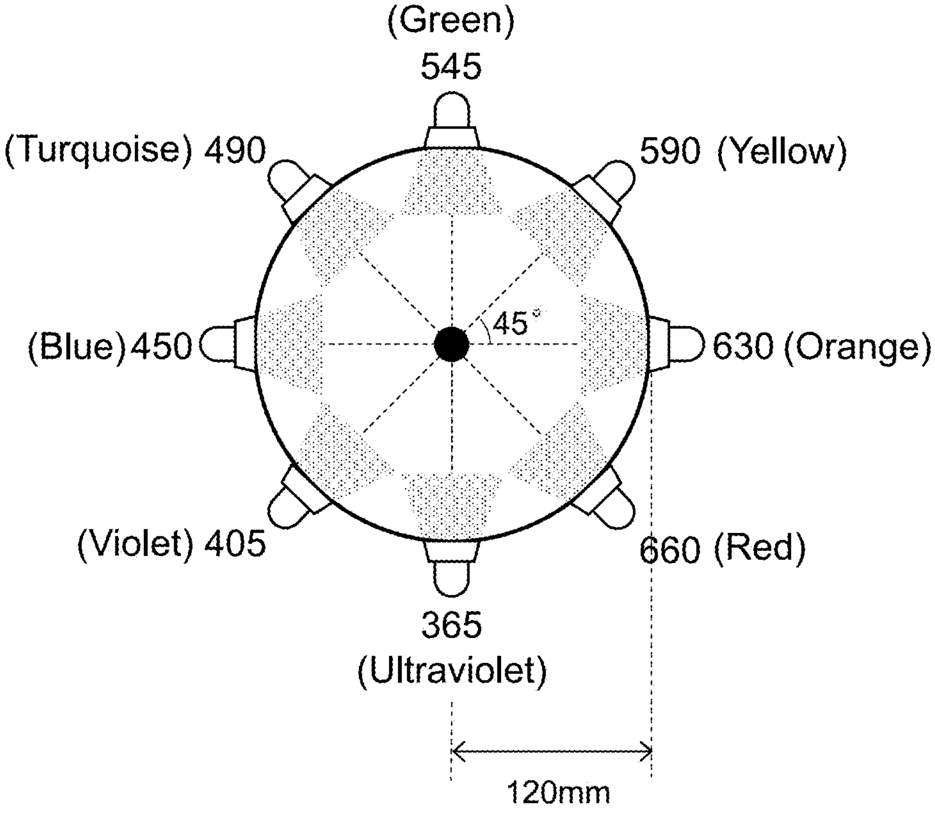
FIG. 1 is a conceptual diagram of a testing device as viewed from above, which was fabricated to examine the wavelength preference of a bagworm as described in Example 1.

1. Method of Controlling Behavior of Bagworm

1-1. Overview

A first aspect of the present invention is a method of controlling a behavior of a bagworm. In a method according to the present invention, radiating a light to a bagworm and changing the direction from which the light is radiated makes it possible to freely control the movement of the bagworm and the direction of the movement, and furthermore, to obtain a bagworm silk thread efficiently.

1-2. Definition of Terms

The following terms frequently used herein are defined as below-mentioned.

The term "bagworm" collectively refers to a moth larva belonging to the family Psychidae in the order Lepidoptera, as described above. Moths belonging to the family Psychidae are distributed worldwide and the larva (bagworm) of any species of the moth spends the whole larval stages living in a nest covered with natural materials, such as pieces of leaves and twigs, which are assembled by silk threads spun by the larva itself. Additionally, any one of the species has the habit of spinning a foothold silk thread which functions as a scaffold in the intended direction of movement to prevent the bagworm from falling when the bagworm moves. Accordingly, the species, instar, and gender of a bagworm used herein are subject to no limitation as long as the bagworm is a larva of a moth species belonging to the family Psychidae, and has the above-mentioned habit. For example, the family Psychidae comprises the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pteroma, Siederia, Striglocyrbasia, Taleporia, Theriodopteryx, Trigonodoma*, and the like. The bagworm used herein may be a species belonging to any genus. Additionally, the instar of the larva may be any instar between the first instar and the last instar. However, a larger bagworm is preferable for the purpose of obtaining a bagworm silk thread. For example, among larvae of the same species, a larva in the last instar is more preferable, and a female larva is more preferable than a male larva because a female grows larger than a male. Furthermore, among the family Psychidae, a larger species is more preferable. For example, *Eumeta japonica* and *Eumeta minuscula*, which are large species, are suitable as species used in the present invention. In principle, a bagworm is a bagworm keeping a nest. "Keeping a nest" refers to the state in which the bagworm has a nest therewith. As above-mentioned, a bagworm usually lives with its own nest. A bagworm exposes only part of the insect body out of the nest even during eating and moving, and the bagworm never exposes its whole body out of the nest throughout the whole larval stage. On the other hand, a bagworm separated from its nest artificially, and placed in a naked state with its whole body exposed outside makes it the first priority to restructure a nest, and thus, has a possibility of not necessarily following the method of controlling the behavior according to the present invention.

The term "bagworm silk thread" as used herein refers to a silk thread spun by a bagworm. The expression "silk thread" as simply used herein refers to a bagworm silk thread, unless otherwise specified. The bagworm silk thread encompasses a monofiber, a spun fiber, and a fiber assembly. The term "monofiber", which is also referred to as a monofilament, is a filament as a smallest unit constituting a fiber component. The monofiber contains a fibroin protein as a main component. The bagworm silk thread in a natural state is spun in the form of a bifilament bonded with a sericin protein as a gummy material. This bifilament is referred to as a "spun fiber". The bagworm nest is constituted by a spun fiber(s). Also, a fiber bundle formed by bundling a plurality of spun fibers is referred to as a "fiber assembly (or multifilament)". In general, this fiber assembly corresponds to raw silk.

There are two kinds of bagworm silk threads: a foothold silk thread and a nest silk thread. As described above, the "foothold silk thread" refers to a silk thread spun by a bagworm for the purpose of its movement, which has a function as a foothold (scaffold) for preventing the bagworm from falling from a branch, a leaf, or the like. On the other hand, the "nest silk thread" refers to a bagworm silk thread spun for forming a nest, which is spun to assemble pieces of leaves and twigs or to make an internal wall of a nest so that its accommodation space becomes a comfortable environment. In view of such a purpose, a foothold silk thread is intended as a bagworm silk thread in the present invention. Thus, the expression "bagworm silk thread" as used herein refers to a foothold silk thread, unless otherwise specified.

As used herein, a "thread mass" refers to a silk thread aggregate composed of a bagworm foothold silk thread(s) alone. The thread mass is not limited to any state. The thread mass may be, for example, in the form of a sheet like an unwoven fabric formed with one or a plurality of bagworm silk threads entangled complicatedly. Without being limited to a two-dimensional shape, the thread mass may also be in three-dimensional shape, having a three-dimensional conformation.

As used herein, a "base material" refers to a base plate for collecting a bagworm silk thread. A bagworm placed on this base material is allowed to move, thus spinning a bagworm silk thread on the surface thereof. After the spinning, collecting the bagworm silk thread from the surface of the base material makes it possible to collect a bagworm foothold silk thread.

As used herein, the term "lead" refers to utilizing the instinctive behavior or the like of an organism to artificially conduct the organism to a specific substance or place.

As used herein, "behavior control" refers to freely manipulating a bagworm's behavior, that is, a motion, such as a movement or a change in the direction.

As used herein, "spinning position control" refers to freely manipulating the spinning behavior of a bagworm so that the bagworm can spin at a predetermined position when spinning a foothold silk thread.

As used herein, a "light" refers mainly to an artificial light radiated from a light source. A "light", as simply used herein, can encompass any light, independent of, for example, the range of the wavelength. For example, the light encompasses any one of the above-mentioned behavior control light and spinning position control light.

As used herein, a "behavior control light" refers to a light having a wavelength that causes the effect of attracting a bagworm. In addition, a "spinning position control light" as used herein refers to a light having a wavelength that restricts the movement of a bagworm, and allows the bagworm to spin a foothold silk thread at a specific position.

As used herein, a "wavelength light" refers to a light having a predetermined wavelength. Accordingly, in the case of the wavelength light, the light is limited to a range of wavelengths to some degree, unlike a light as simply used herein. However, the range does not need to be specific.

As used herein, a "light having a peak in the wavelengths" refers to a wavelength light having a peak wavelength.

Figure 2:
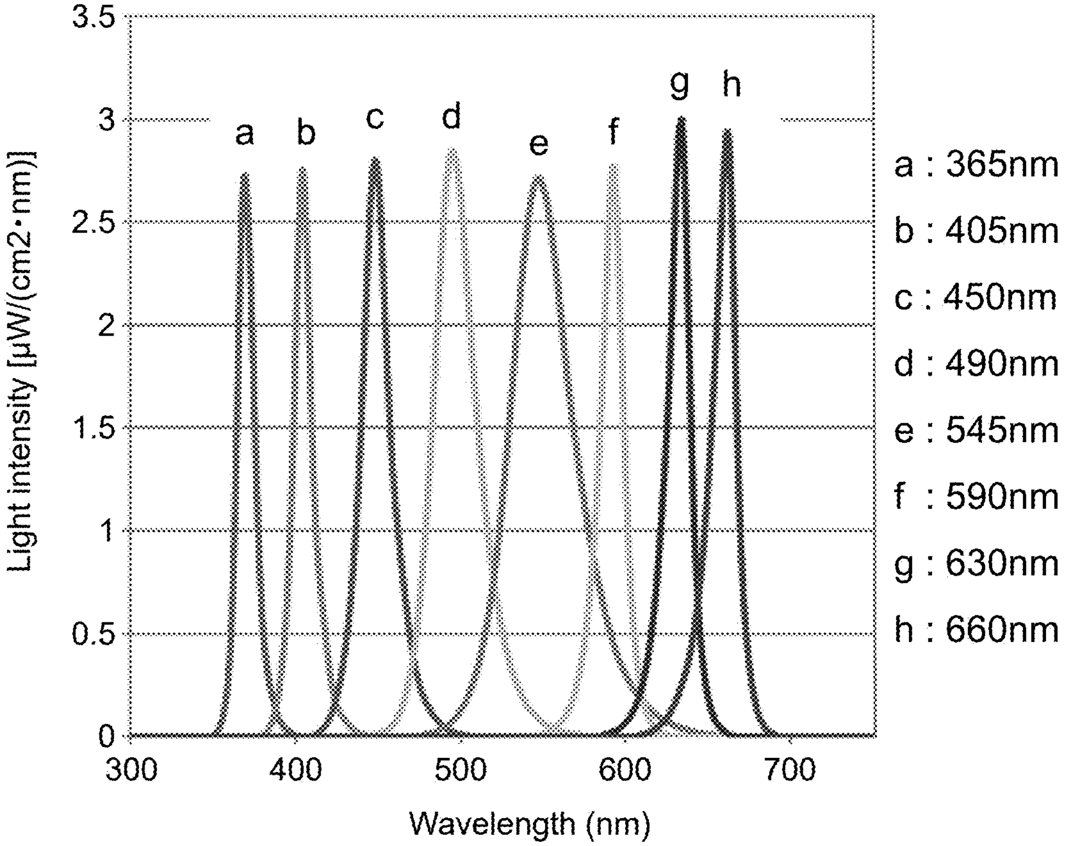
FIG. 2 is a graph showing the wavelength and light intensity of each light source used for the testing device in FIG. 1.

As shown by "a" to "h" in FIG. 2, a "peak wavelength" as used herein refers to a wavelength of a radiated light, at which wavelength the light intensity reaches the maximum value (peak) in the wavelengths of the light that describe a mountainous shape. In addition, a light in such a condition, that is, a wavelength light at a peak wavelength is herein often referred to as a "peak light".

1-3. Method

A method in the present aspect comprises a leading process as an essential process and a directional control process as an optional process. Each of the processes will be specifically described below.

1-3-1. Leading Process

A "leading process" is a process of radiating a behavior control light to a bagworm to lead the bagworm toward the direction of light radiation. This process is a process of utilizing phototaxis by which a bagworm moves toward the direction of light radiation.

The behavior control light may be a light having a wavelength in response to which a bagworm exhibits positive phototaxis, and the light is not limited to any particular wavelength or light intensity. To lead a bagworm toward the direction of light radiation more efficiently, a specific wavelength light is preferably radiated as a behavior control light.

In a case in which a "specific wavelength light" in this process (herein often referred to as a "specific wavelength light") is a behavior control light, the specific wavelength light refers to a wavelength light having a strong attracting effect on a bagworm. Specifically, a wavelength light having a wavelength in the range of 405 nm±60 nm (345 nm or more and 465 nm or less), 405 nm±55 nm (350 nm or more and 460 nm or less), or 405 nm±50 nm (355 nm or more and 455 nm or less) is applied. The wavelength light preferably has a peak wavelength in these wavelength ranges. As shown in the below-mentioned Example 1, a wavelength light in these ranges has a strong attracting effect on a bagworm, compared with other wavelength lights.

In a case in which the specific wavelength light has a peak wavelength, the light may be any one of a single-color light having one peak wavelength in the specific wavelength range and a complex light having a plurality of peak wavelengths in the wavelength range. The single-color light is preferable.

"Radiating a light (to a bagworm)" refers to radiating, to a bagworm, any wavelength light, for example, a wavelength light in the range of 405 nm±60 nm, 405 nm±55 nm, or 405 nm±50 nm, if the light is a behavior control light. Even if a light, such as the light of a fluorescent lamp, which has no peak wavelength, is radiated, it is possible that the light is allowed to pass through a wavelength selection filter in order to produce only a wavelength light in the range selectively transmitted, and thus that the wavelength light transmitted is radiated as a specific wavelength light. In this regard, "radiating to bagworm" refers to causing an eye(s) as a photoreceptor of a bagworm or the head having the eye(s) to be directly exposed to the light.

A "direction of light radiation" refers to a direction from which a light is radiated. For example, in the case of the below-mentioned direct radiation, the direction corresponds to the direction in which a light source is mounted. In addition, in the case of indirect radiation, the direction corresponds to the direction of the plane of reflection of a reflective material.

The radiation of a light to a bagworm is preferably continuous radiation, but may be intermittent radiation, for example, a pulse light that repeats light and dark periods in an extremely short time, examples of which pulse light comprise a light from a fluorescent lamp; or radiation in which a dark period that can be recognized with naked eyes cyclically or acyclically in a period of radiation (for example, a dark period of one second or more, preferably several seconds) is inserted.

The method of radiating a light to an object is subject to no particular limitation as long as the method makes it possible to radiate a light to a bagworm as the object. For example, the method may be any one of direct radiation and indirect radiation. Direct radiation refers to directly radiating, to a bagworm, a light radiated from a light source. In direct radiation, a light can be radiated with the light source directed toward a bagworm. In the case of direct radiation, the bagworm moves toward the direction in which the light source is mounted. In addition, indirect radiation refers to allowing a light to be reflected by a reflective material or the like, followed by radiating the reflected light to a bagworm, without directly radiating, to the bagworm, a light radiated from the light source. Indirect radiation may involve allowing a light radiated from a light source to be reflected by a reflective material, such as a mirror, followed by radiating the light toward a bagworm. Indirect radiation may be performed through reflecting a light a plurality of times using a plurality of reflective materials. In indirect radiation, attention should be paid so that the reflected light radiated to a bagworm can be the specific wavelength light. Indirect radiation is useful particularly in a case in which a light should be radiated to a bagworm from a specific direction using a fixed light source.

The time during which a light is radiated to a bagworm is subject to no particular limitation. In a case in which a bagworm is led to a predetermined position, the above-mentioned behavior control light may be radiated to the bagworm, but after the bagworm finishes moving to the predetermined position, further radiation of the behavior control light is usually unnecessary. On the other hand, in a case in which a bagworm moves to a predetermined position, and is then held around the position, and in addition, is allowed to spin actively at the position, the spinning position control light may subsequently continue to be radiated to the bagworm at the position, as described in the below-mentioned second aspect.

In this process, the number of bagworms per treatment with light radiation is subject to no particular limitation. As long as a bagworm(s) is/are placed in a light radiation area, the species, number of individuals, and/or instar of the bagworm(s) are subject to no limitation. In a case in which a plurality of bagworms are placed, for example, all the individuals may be of the same species and/or of the same instar, or a group of part of the individuals may be of the same species and/or of the same instar.

This process makes it possible to lead a bagworm toward a predetermined direction, and thus, without being limited to a collection purpose, can be also utilized, for example, to allow a bagworm to efficiently move from an old feeding ground to a new feeding ground to feed the bagworm in a rearing environment.

1-3-2. Directional Control Process

The "directional control process" is a process of changing the direction of movement of the bagworm by changing the direction of light radiation. As above-mentioned, when a light is radiated to a bagworm, the bagworm moves toward the direction of light radiation. Even if a bagworm is on the way in movement, any shift in the direction of light radiation changes the direction of movement in accordance with the shift. This makes it possible to freely control the direction in which the bagworm moves.

A means of changing the direction of light radiation is subject to no particular limitation. In the case of direct radiation, a light source may be mounted in a new direction in which a bagworm is to be moved. In a case in which a light source is not movable, a base material itself on which a bagworm is placed may be moved so that the base material can be turned toward the light source in a predetermined direction. In addition, in the case of indirect radiation, it is possible that a reflective material is moved and/or rotated, and, if desired, the number of the reflective materials is increased or decreased so that a light can be radiated to a bagworm from a predetermined position on the base material(s).

The direction of light radiation is subject to no limitation. A predetermined direction in which a bagworm is to be led is the direction of light radiation. In addition, the direction of light radiation may be changed once or a plurality of times, if desired.

Using the present process in combination with the leading process makes it possible to freely control the behavior of a bagworm, for example, lead a bagworm toward a predetermined direction in a rearing container or in a thread-producing apparatus.

2. Method of Controlling Spinning Position of Bagworm

2-1. Overview

A second aspect of the present invention is a method of controlling a spinning position of a bagworm. The present invention is based on the new discovery that, when a light different in the main wavelength range from a behavior control light is radiated to a bagworm from a predetermined position, the spinning behavior of the bagworm at the predetermined position is promoted. A method in this aspect is also an embodiment of a method of collecting a bagworm silk thread.

The method of controlling a spinning position of a bagworm according to the present invention makes it possible to allow the bagworm to spin at a predetermined position on a base material. Furthermore, using the present method in combination with a method of controlling the movement of a bagworm in the first aspect makes it possible to lead a bagworm to a predetermined position, and allow the bagworm to spin at the position.

2-2. Method

A method in the present aspect comprises a spinning process as an essential process and a leading process and a directional control process as optional processes. Each of the processes will be specifically described below.

2-2-1. Spinning Process

The "spinning process" is a process of radiating a spinning position control light to a bagworm from a predetermined position, and allowing the bagworm to spin at the position. In a case in which a bagworm is irradiated with the spinning position control light, the spinning at the position exposed to light is promoted. This process utilizes this characteristic.

The wavelength and light intensity of the spinning position control light are subject to no particular limitation. To allow a bagworm to spin more efficiently, a specific wavelength light is preferably radiated as a spinning position control light. A specific wavelength light as used herein refers to a wavelength light having a high spinning effect on a bagworm. The specific wavelength light in this process may be the same wavelength light as, or a different wavelength light from the specific wavelength light used in a method of controlling the movement of a bagworm in the first aspect. The spinning position control light is preferably a wavelength light having a high spinning effect. Specifically, a wavelength light that applies here has a wavelength in the range of 560 nm±150 nm (410 nm or more and 710 nm or less), 560 nm±140 nm (420 nm or more and 700 nm or less), 560 nm #130 nm (430 nm or more and 690 nm or less), 560 nm±120 nm (440 nm or more and 680 nm or less), or 560 nm±110 nm (450 nm or more and 670 nm or less). The basic constituents other than the wavelength that are related to the spinning position control light are in accordance with the basic constituents of the specific wavelength light in the leading process in the first aspect. For example, the radiating condition and the light-shielding condition may be achieved in accordance with the leading process in the first aspect. Thus, the description of the duplicate characteristics is omitted here.

In this process, the "predetermined position" refers to a position at which a bagworm is allowed to spin. The position usually refers to a position of interest on the surface of a base material on which a bagworm is allowed to spin. In a method of controlling a spinning position of a bagworm according to the present invention, a bagworm may be placed at a predetermined position, or a bagworm may be led to a predetermined position from another place in accordance with the below-mentioned leading process and directional control process so as to be placed at the position. As used herein, the phrase "a bagworm . . . placed" refers to the disposition of a bagworm at a predetermined position for the purpose of collecting a bagworm silk thread.

The number of individual bagworms to be placed in this process is subject to no limitation. For example, one bagworm or a plurality of bagworms may be placed at a predetermined position. Additionally, the bagworm to be placed is not limited to any species or instar. In a case in which a plurality of bagworms are placed, the individuals may be of the same species and/or of the same instar, or may be of different species and/or of different instars.

This process is not limited to any particular period of time. The process period depends on the species, instar, and number of an individual bagworm(s) to be used, but in any case, the process may be continued until a necessary amount of thread is spun at a predetermined position. For example, in a case in which one last instar *Eumeta japonica* bagworm is used to spin a thread on a circular base material having a diameter of 9 cm as a predetermined position, the bagworm is allowed to spin for 1 day or more, 2 days or more, 3 days or more, 4 days or more, 5 days or more, 6 days or more, or 7 days or more. As described above, the bagworm foothold silk thread is spun while the bagworm moves, and thus, the amount of the silk thread obtained is in proportion to the moving distance of the bagworm in principle. Because of this, allowing a plurality of bagworms to spin takes a shorter spinning process time than allowing a single bagworm to spin. Additionally, the bagworm is not allowed to eat food while spinning, and thus, the bagworm often stops spinning in this process. In such a case, it is also possible to exchange the bagworm for a new one, which can take over the spinning process.

It is recommended that the temperature and humidity in this process are constant or change less so that the amount of thread spun by a bagworm per unit time can be larger. It is preferable that the temperature is around 25° C., for example, ranges from 20° C. to 30° C., or from 23° C. to 27° C., and that the humidity is around 50%, for example, ranges from 40% to 65%, or from 45% to 60%. The light and dark periods during this process are subject to no particular limitation, and the process may have only a light period, or may have cyclical light and dark periods. For example, the cycle may be such that, in 24 hours, the light period is 6 hours to 18 hours, 7 hours to 17 hours, 8 hours to 16 hours, 9 hours to 15 hours, 10 hours to 14 hours, 11 hours to 13 hours, or 12 hours, and the rest is the dark period.

A material constituting a base material on which a bagworm is placed is subject to no particular limitation as long as a bagworm silk thread can be fixed on the surface of the base material when the bagworm moves. Examples thereof comprise glass (comprising enamel), metal, a synthetic resin (comprising a thermoplastic resin, a thermosetting resin, and a synthetic rubber), ceramic, paper, a piece of plant (comprising, for example, a piece of wood), or a piece of animal (comprising, for example, a piece of bone, seashell, and sponge). Examples of the synthetic resin comprise polyethylene, polypropylene, polystyrene, vinyl acetate, cellulose acetate, acryl resins, and polycarbonate, and the like. Considering that the present invention is a method of controlling the behavior of a bagworm, such as the movement and spinning thereof, by light radiation, the base material is preferably a transparent base material or a translucent base material. The transparent base material refers to a base material that has a very high light transmittance, and has a quality that enables an object present in the opposite side of the base material to be seen through the base material. Examples of the transparent base material comprise glass, polyethylene, polystyrene, acryl resin, and the like. The translucent base material refers to a base material having a quality that allows the base material to transmit a light, but that causes the light transmittance to be low, with the result that the shape or the like of an object present in the opposite side of the base material cannot be clearly recognized, or can hardly be recognized, through the base material. Examples of the translucent base material comprise polypropylene, frosted glass, and the like.

The base material is not limited to any thickness. The thickness can suitably be determined taking into account the production cost and rigidity of the base material, the ease of processing in the subsequent processes, and the like. For example, the average thickness of the base material is preferably 0.5 mm or more, 0.6 mm or more, 0.7 mm or more, 0.8 mm or more, 0.9 mm or more, 1.0 mm or more, 1.2 mm or more, or 1.5 mm or more, and additionally, may be 3.0 mm or less, 2.8 mm or less, 2.5 mm or less, 2.2 mm or less, or 2.0 mm or less. In a case in which the base material is composed of a thin film having an average thickness of less than 0.5 mm, 0.4 mm, 0.3 mm, 0.2 mm, or 0.5 mm, the base material itself does not have enough rigidity to retain a given shape, and thus, the base material may be placed on a suitable support.

As used herein, a "support" refers to a member that can give rigidity and/or a shape to the base material. The base material is usually placed on the surface of the support. The support is not limited to any particular material as long as the material has enough rigidity to retain a given shape. Examples thereof comprise glass, metal, plastic, synthetic rubber, ceramic, paper, a piece of plant, or a piece of animal. Considering the characteristics of the present invention, the support is also preferably a transparent material or a translucent material as with the base material.

A base material used in this process is not limited to any shape or size. The shape may be, for example, a planar shape, such as a sheet-like or plate-like shape, a simple or complicated three-dimensional shape, or a combination thereof. The present invention also makes it possible for a bagworm to spin on the whole surface of a base material even if the base material is a three-dimensionally-shaped material (three-dimensional structure) on which it is usually difficult to spin. The size of the base material can also be a size that is selected as necessary, and in view of the fact that the foothold silk thread is a bagworm silk thread spun during moving, the lower limit is preferably a size equal to or greater than the body length of the bagworm. For example, the long axis or the long diameter can be 1 cm or more, 2 cm or more, 3 cm or more, 4 cm or more, or 5 cm or more. On the other hand, the size of the base material is not limited to any upper limit, and in a case in which the long axis or the long diameter is 10 cm or more, 15 cm or more, 20 cm or more, 25 cm or more, or 30 cm or more, it is more preferable to allow a plurality of bagworms to spin threads.

2-2-2. Leading Process and Directional Control Process

The leading process and the directional control process in the present invention are optional processes in a method of controlling a spinning position of a bagworm. The description of the specific procedures and the like for these processes is in accordance with the description of the leading process and the directional control process in the method of controlling the movement of a bagworm in the first aspect.

In the method of controlling a spinning position of a bagworm in this aspect, the spinning process that is an essential process makes it possible to allow a bagworm to spin a foothold silk thread at a predetermined position. However, in a case in which a spinning position control light is radiated to a bagworm, the spinning behavior of the bagworm is led, with the result that the movement of the bagworm is restricted. Accordingly, for a bagworm to complete spinning at a predetermined position, and subsequently spin at the next predetermined position, the method of controlling the behavior of a bagworm in the first aspect can be incorporated in the method in the present aspect. That is, the radiated light is switched from the spinning position control light to the behavior control light after the spinning process, and the light is radiated to a bagworm with the direction of light radiation controlled to a new predetermined position of interest, whereby the bagworm can be led to the new predetermined position. After the bagworm reaches the new predetermined position, the radiated light can be switched from the behavior control light to the spinning position control light again so that the spinning behavior can be led at the position. Repeating this makes it possible to lead spinning continuously even in a case in which there are a plurality of predetermined positions at each of which a foothold silk thread is to be spun.

In a method of controlling a spinning position of a bagworm according to the present invention, the leading process and the directional control process may be followed or preceded by the spinning process. The order is not subject to any limitation.

2-3. Effect

A method of controlling a spinning position of a bagworm according to the present invention makes it possible to spin a foothold silk thread at a specific position on the surface of a base material having any shape, regardless of a planar structure or a three-dimensional structure of the base material. In addition, the method makes it possible to spin on the whole surface of a three-dimensional structure having a complicated shape. As a result, a thread mass having a desired three-dimensional shape and formed of bagworm silk threads composed of foothold silk threads can be produced. Such a thread mass can also be made into a complicated shape that cannot be produced even by pressing a sheet-like bagworm silk thread. In addition, a base material to be used for a method of producing a bagworm silk thread may be made of a raw material soluble in a solvent that does not damage a bagworm silk thread physically or chemically. In this case, dissolving the base material in the solvent after the spinning process also makes it possible to produce a thread mass constituted by bagworm silk threads alone and having a desired shape. Such a thread mass can be utilized, for example, for a scaffold material in regenerative medicine.

3. Bagworm Silk Thread-Producing Apparatus

3-1. Overview

A third aspect of the present invention is a bagworm silk thread-producing apparatus. A bagworm silk thread-producing apparatus according to the present invention is an apparatus that embodies a method of controlling a spinning position of a bagworm in the second aspect. Placing a base material as an object for spinning in the apparatus makes it possible to allow a bagworm to spin a foothold thread at a predetermined position on the base material.

3-2. Configuration

A bagworm silk thread-producing apparatus according to the present invention comprises a first light source as an essential constituent, and comprises a second light source and/or a housing as an optional constituent(s). Below, each constituent will be specifically described.

3-2-1. First Light Source

The "first light source" is a spinning position control light as described in a method of controlling a spinning position of a bagworm in the second aspect, and is specifically a light source that can radiate a light in the range of visible light of 560 nm±150 nm, 560 nm±140 nm, 560 nm±130 nm, 560 nm±120 nm, or 560 nm±110 nm, which has a high spinning effect on a bagworm. In the apparatus according to the present invention, the first light source is configured such that the first light source can radiate a light from any direction to a base material placed in the apparatus. The first light source can also be used as a light source for controlling a spinning position of a bagworm.

The first light source is subject to no particular limitation as long as the light source can radiate a wavelength light in the above-mentioned range of wavelengths. Examples of a preferable light source comprise an LED. The wavelength spectrum of an LED describes a waveform having a peak light at a specific wavelength, and thus, such a light source is preferable in the present invention. However, as above-mentioned, even a light source that radiates a light having no peak wavelength, such as a fluorescent lamp or a mercury lamp, can be used if the light source can radiate, as the spinning position control light, only a transmitted light selected through a wavelength-selective filter.

The apparatus may comprise at least one first light source or a plurality of first light sources. In the case of a plurality of first light sources, the light sources may be mounted so as to be directed in the same direction toward a base material, or may be mounted so as to be directed in different directions toward the base material. In addition, as long as the light sources are light sources which can radiate a wavelength light in the above-mentioned range of wavelengths, the light sources may be light sources which can radiate different wavelength lights, for example, different wavelength lights having different peak wavelengths.

In a case in which the apparatus comprises a plurality of first light sources, the light sources may be configured such that the light sources can radiate a light simultaneously or at different times.

The first light source may be movable. For example, a light source is mounted on a flexible arm disposed in the apparatus so that the light source can radiate a light from any direction to a base material to be placed in the apparatus. Alternatively, a rail is mounted in the apparatus, and configured such that a light source can move on the rail.

The spinning position control light emitted from the first light source may be configured to be directly radiated to a base material to be placed in the apparatus, or may be configured to be indirectly radiated to the base material through one or a plurality of reflective materials. In this case, the apparatus can comprise one or a plurality of reflective materials. Each reflective material may be configured such that the reflection angle can be changed to adjust the position at which a light is reflected.

3-2-2. Second Light Source

The "second light source" is a light source that can radiate a behavior control light as described in a method of controlling the movement of a bagworm in the first aspect, specifically a wavelength light in the range of 405 nm±60 nm, 405 nm±55 nm, or 405 nm±50 nm. In the apparatus according to the present invention, the second light source is configured such that the second light source can radiate a light from any direction to a base material to be placed in the apparatus to allow a bagworm to move to any position on the base material. The second light source can also be used as a light source for controlling the behavior of a bagworm.

The first light source and the second light source can also be the same light source. In this case, the light source can be configured such that the light source can radiate a wavelength light in the range of wavelengths that allow both the leading effect and the spinning effect to be the highest. For example, the wavelength light comprises the wavelength light in the range of 410 nm or more and 465 nm or less.

The basic configuration of the second light source is basically the same as the configuration of the first light source except that the range of a wavelength light to be radiated is different. Thus, the description of the basic configuration of the second light source is omitted here.

3-2-3. Housing

The "housing" is a constituent member that provides a light-shielding environment for a bagworm silk thread-producing apparatus according to the present invention, and is an optional constituent of the apparatus. The light-shielding environment is usually provided inside the housing. Accordingly, the housing in the apparatus is configured such that at least a bagworm and a base material for spinning can be placed inside the housing. The first light source or the second light source or the reflective material thereof may be mounted inside the housing.

3-2-4. Base Material

The "base material" is not a constituent of a bagworm silk thread-producing apparatus according to the present invention, but a member to be supplied to the apparatus. The material, shape, and the like of the base material are in accordance with those of the base material in the description of the spinning process in a method of controlling a spinning position of a bagworm in the second aspect.

3-3. Effect

A bagworm silk thread-producing apparatus according to the present invention is an invention in the form of an apparatus that embodies a method of controlling a spinning position of a bagworm in the second aspect. Placing a base material as a spinning objective and a bagworm in the apparatus, followed by operating the apparatus, makes it possible to allow the bagworm to spin a foothold thread at a predetermined position on the base material. This apparatus makes it possible to spin at a predetermined position on the surface of the base material having a complicated three-dimensional structure.

EXAMPLES

Example 1: Examination of Wavelength Light that Leads Bagworm

Purpose

To verify how bagworms are led by a light, different wavelength lights having different wavelength peaks respectively are simultaneously radiated from side faces to the bagworms to verify by which wavelength light the bagworms are led.

Method

As bagworms, 20 last instar *Eumeta minuscula* larvae having the same size were used.

A testing device was produced with reference to a testing device developed for the purpose of examining the wavelength preference of a Pentatomidae insect (Takumi Ogino, et al., 2015, The Japanese Journal of Applied Entomology and Zoology, 59:10-13). In the device, eight light sources for different wavelengths were attached at angle intervals of 45° on the side of a cylindrical container the whole face of which was constituted by a light-shielding raw material, and which had a radius of 120 mm and a height of 30 mm (FIG. 1). As light sources, LEDs having peak wavelengths at (a) 365 nm (an ultraviolet light), (b) 405 nm (a violet light), (c) 450 nm (a blue light), (d) 490 nm (a turquoise light), (e) 545 nm (a green light), (f) 590 nm (a yellow light), (g) 630 nm (an orange light), and (h) 660 nm (a red light) respectively were used (FIG. 2). The LEDs used exhibited almost no difference in light intensity thereamong, as shown in FIG. 2. The bagworm was placed in a concave region which is provided in the central portion of the testing device and has a diameter of 15 mm and a depth of 60 mm. Then, the 8 light sources were lighted simultaneously, and which light source the bagworm first reached was examined. The same test was repeated on the 20 different bagworms. The number of bagworms that reached each wavelength light was measured.

Results

Figure 3:
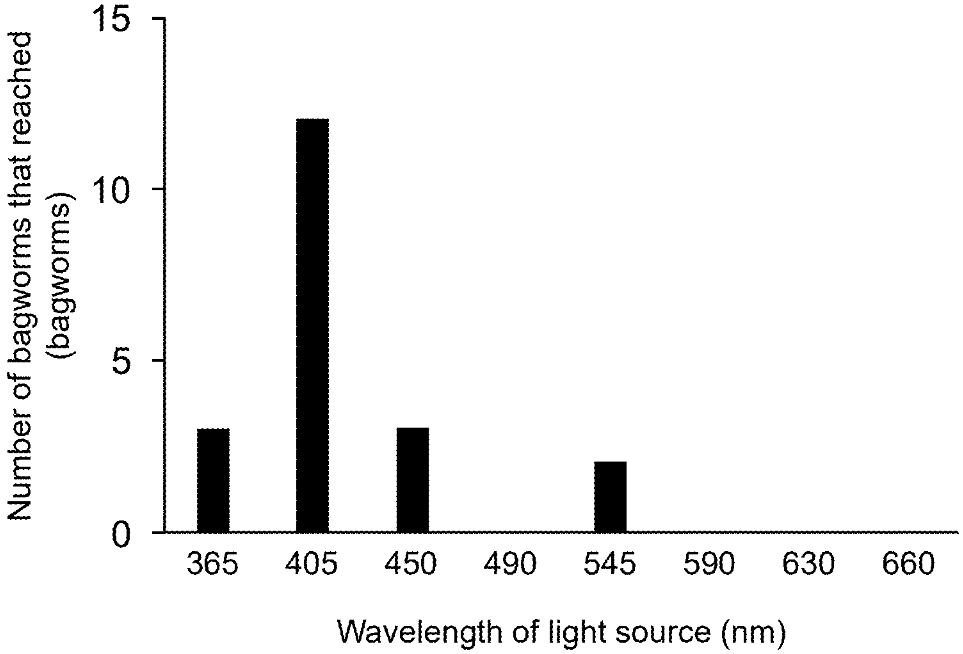
FIG. 3 is a graph showing the number of bagworms that reached each light source in the experiment in Example 1 in which the testing device in FIG. 1 was used.

FIG. 3 shows the number of bagworms that reached each light source wavelength. As shown in FIG. 3, in a case in which the respective wavelength lights were radiated simultaneously, more bagworm individuals were led to shorter-wavelength lights than to longer-wavelength lights. However, the result has revealed not that the bagworms were led more strongly to a shorter wavelength, but that the range of wavelengths within the range of 405 nm plus and minus 60 nm was the most effective. This result suggests that radiating a behavior control light at 405 nm±60 nm to a bagworm makes it possible to lead the bagworm toward the direction of light radiation.

Example 2: Behavior Control and Spinning Position Control Toward Desired Face of Three-Dimensional Structure Purpose Example 1 verified that radiating a behavior control light made it possible to lead a bagworm toward the direction of light radiation of the behavior control light effectively. This Example verified whether radiating a spinning position control light to a bagworm made it possible to produce a thread mass at a predetermined position of a three-dimensional structure efficiently.

Materials and Method

As bagworms, last instar *Eumeta minuscula* larvae having the same size were used.

Figure 4:
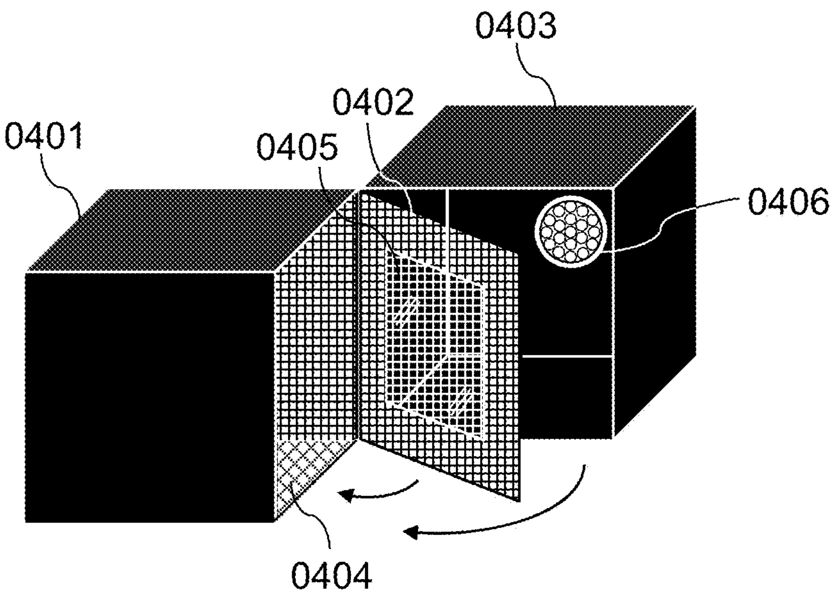
FIG. 4 is a conceptual diagram of a testing device fabricated to verify whether the spinning position can be controlled with light radiation in a three-dimensional structure.
Figure 4:
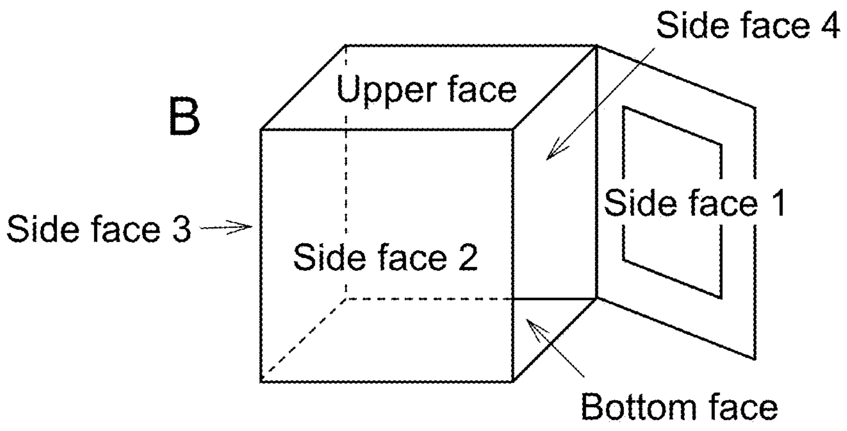
Figure 5:
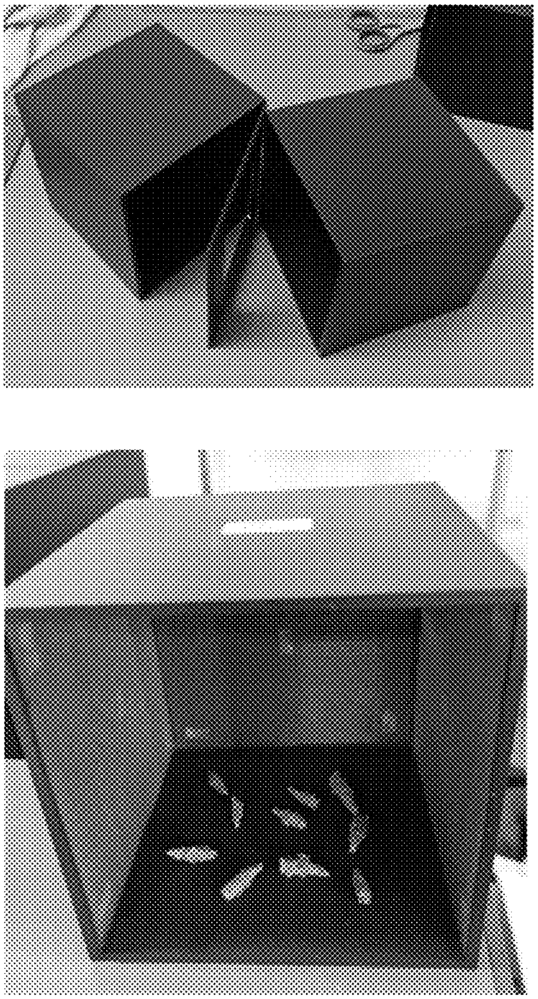
FIG. 5 is an actual image of the testing device in FIG. 4.

For the test, a device shown in FIG. 4 was used. As shown in FIG. 4A, this device was composed of four main parts: two cubes (cages 0401 and 0403) each constituted by a light-shielding non-reflective member, 100 mm on a side; a light-shielding non-reflective square plate (0402), 100 mm, on a side; and light sources (0406). The square plate (0402) had a large square window (0405) in the central portion thereof. To this window, the below-mentioned nylon-made mesh was attached. The two cubes (0401 and 0403) were each in the form of a box having six faces of which one face was open, and were configured to have the square plate (0402) therebetween so that the respective opening faces could be opened and closed. In a case in which the opening faces were closed, the inside spaces of the two cubes (0401 and 0403) were isolated from each other by the square plate (0402), whereby two dark rooms were formed. A bagworm was placed in one (0401) of the cages. To all the six inner wall faces of the cage in which a bagworm was placed, nylon-made meshes (0404) for assisting the bagworm in moving were attached. The other cage had the light sources (0406) on the face opposite from the opening face, and was configured such that a light could be radiated to the inside space. The light emitted from the light source with the opening face closed reached the inside of the cage (0401) through the window (0405). Thus, only the light-radiating face was a face through which a light could enter the inside of the cage. The faces other than that completely blocked a light, and allowed no entry of a light from the outside. In addition, the non-reflective member prevents a light entering from the light-radiating face from being reflected by each face. The above-mentioned operation constructed a test system that made it possible to radiate a light from the LED light source at a distance of 100 mm from the light-radiating face of the cubic cage (0401). As light sources, 8 types were provided, as follows: an ultraviolet LED (the maximum wavelength, 365 nm), a violet LED (ditto, 405 nm), a blue LED (ditto, 450 nm), a turquoise LED (ditto, 490 nm), a green LED (ditto, 545 nm), a yellow LED (ditto, 590 nm), an orange LED (ditto, 630 nm), and a red LED (ditto, 660 nm). As a negative control, a dark experiment section having no light source mounted therein was added. Under the 9 types of conditions in total, the weight of a bagworm thread mass was compared among the faces. Every 2 to 4 days, 10 bagworms placed were replaced with new bagworms that had been sufficiently fed preliminarily. The experiment was continued for 13 days in total. During the experiment, the temperature was held at 26° C. in the test system. On the thirteenth day after the experiment started, bagworm thread masses spun on the side faces were collected, and the weight of the thread masses on each face was measured. As shown in FIG. 4B, the side faces are as follows: the "side face 1" as a light-radiating face; and the "side faces 2 to 4" clockwise as viewed from above.

In this regard, the weight of the thread masses on the upper face was measured only under the dark conditions as a negative control, but the bottom face was not regarded as a measuring object. The reason in relation to the upper face is that the below-mentioned results have revealed that the instinctive characteristic by which a bagworm prefers a higher place is maintained also in the dark, thus allowing the bagworm to spin at the upper face irrespective of optical leading. In addition, the reason in relation to the bottom face is that the bottom face is the first place where a bagworm is placed, and where the bagworm also spins at the bottom face irrespective of optical leading when the bagworm moves toward one of the side faces.

Results

Under the dark conditions as a negative control, the result was that the weight of the thread masses on the upper face was the most, compared with the four side faces (the data are not shown). This is due to the instinctive characteristic by which a bagworm tends to move to a higher place, and stay at the place. In view of this, to eliminate the influence of the upward movement of a bagworm, and compare only the influence of the wavelength of a light on the spinning behavior, the ratio of the weight of the thread masses on the light-radiating face (side face 1) to the average weight of the thread masses on the other three side faces (side faces 2, 3, and 4) was calculated. Thus, the respective wavelength lights were compared.

Figure 6:
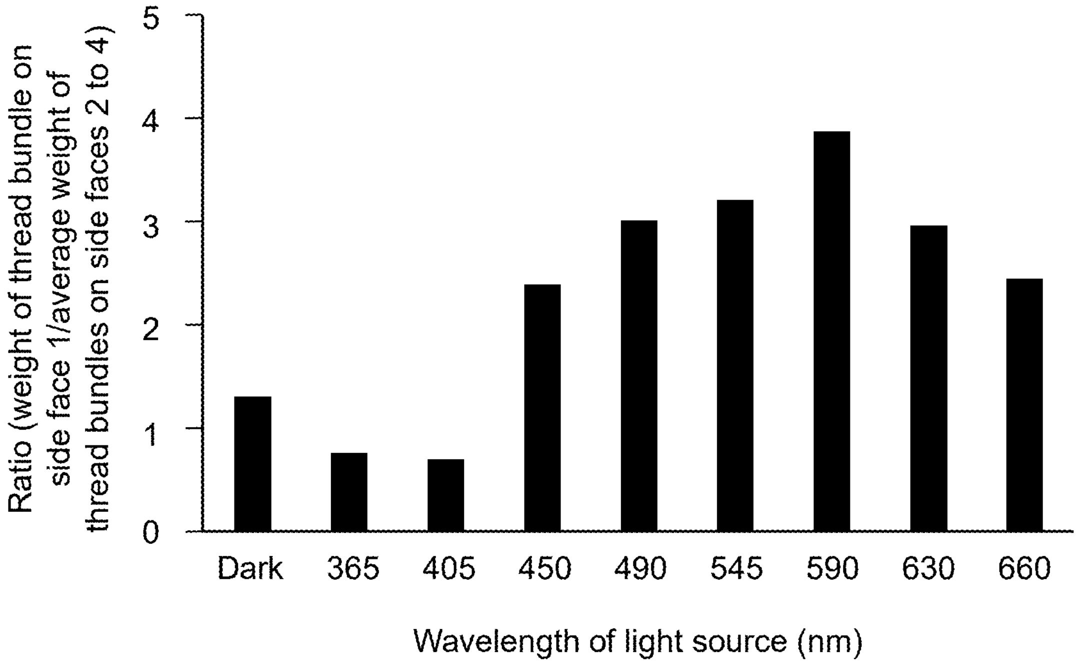
FIG. 6 is a graph showing the ratio of the weight of a thread mass on the light-radiating face (a side face 1) to the average weight of thread masses on the non-radiating side faces (side faces 2 to 4) regarding each light source in Example 2.

The results are shown in FIG. 6. The results have verified that, under the light radiation conditions, the weight of the thread masses on the side face 1 as the light-radiating face was twice or more as large as the average weight of the thread bundles on the other side faces, except during the radiation of the short wavelength light at 365 nm and 405 nm. Surprisingly, the ratio by weight of the thread masses on the side face 1 was contrarily the lowest value when the wavelength light at 405 nm, at which the bagworm was led the most strongly in Example 1, was radiated. In contrast, the ratios by weight of the thread bundles on the side face 1 were high values when wavelength lights at 450 nm to 660 nm were radiated. This result suggests that the wavelength of a behavior control light having a high leading effect and the wavelength of a spinning position control light having a high spinning effect are not necessarily equal.

The above-mentioned results have revealed that the present invention makes it possible that radiating a behavior control light from a desired position on a three-dimensional structure allows a bagworm to be led to the position, and then, that switching the light to a spinning position control light at the position, followed by radiating the latter light, allows a thread bundle to be formed efficiently at the desired position.

All publications, patents, and patent applications cited herein should be incorporated herein by reference in their entirety.

The invention claimed is:

1. A method of controlling behavior of a bagworm, comprising a process of radiating a behavior control light to the bagworm to lead the bagworm toward a direction from which the light is radiated, wherein a wavelength of the behavior control light is 405 nm±60 nm.

2. The method of claim 1, the method further comprising changing the direction from which the light is radiated.

3. The method of claim 1, which is performed under a light-shielding condition.

4. A method of controlling a spinning position of a bagworm, comprising a process of radiating a spinning position control light from a predetermined position toward the bagworm to restrict movement thereof on a base material to induce the bagworm to spin a foothold silk thread at the position, wherein a wavelength of the spinning position control light is 490 nm to 710 nm.

5. The method of claim 4, further comprising a process of radiating a behavior control light having a wavelength of 405 nm±60 nm to the bagworm from the predetermined position on the base material to lead the bagworm to the position.

6. The method of claim 4, which is performed under a light-shielding condition.

7. The method of claim 4, wherein the base material is a three-dimensional structure.

8. The method of claim 4, wherein the base material is a transparent base material or a translucent base material.

9. A method of producing a thread mass of a bagworm silk thread obtained using the method of controlling the spinning position of the bagworm according to claim 4.

10. A bagworm silk thread-producing apparatus comprising a three-dimensional base material, one or a plurality of movable light sources that can radiate a spinning position control light having a wavelength of 490 nm to 710 nm from any direction to the three-dimensional base material, one or a plurality of movable light sources that can radiate a behavior control light having a wavelength of 345 nm to 465 nm from any direction to the three-dimensional base material, a housing providing a light-shielding environment.

11. A system for producing bagworm silk thread by one or more bagworms, comprising:

a bagworm silk thread-producing apparatus, the apparatus comprising:

a cage for containing one or more bagworms, a base material in the cage on which a bagworm is allowed to spin;

one or a plurality of light sources that can radiate a spinning position control light restricting the movement of the bagworm from any direction on the base material, that radiates from 490 nm to 710 nm;

one or a plurality of light sources that can radiate a behavior control light, that radiates from 345 nm to 465 nm;

a light shielded zone within the apparatus;

wherein a bagworm placed in the cage is guided to a predetermined position on the base material where the bagworm anchors a foothold thread; and then the bagworm is guided to continue spinning in a predetermined direction by the behavior control light.

* * * * *